US010907001B2

(12) United States Patent
Coury et al.

(10) Patent No.: US 10,907,001 B2
(45) Date of Patent: Feb. 2, 2021

(54) BIOSTABLE SEGMENTED ELASTOMERS AND THERMOPLASTICS AND METHODS OF MAKING AND USING THEREOF

(71) Applicants: The Arizona Board of Regents on Behalf of The University of Arizona, Tucson, AZ (US); Arthur J. Coury, Boston, MA (US)

(72) Inventors: Arthur J. Coury, Boston, MA (US); Marvin J. Slepian, Tucson, AZ (US)

(73) Assignees: The Arizona Board of Regents on Behlaf of the University of Arizona, Tucson, AZ (US); Arthur J. Coury, Tucson, AZ (US)

( * ) Notice: Subject to any disclaimer, the term of this patent is extended or adjusted under 35 U.S.C. 154(b) by 95 days.

(21) Appl. No.: 15/760,830

(22) PCT Filed: Sep. 19, 2016

(86) PCT No.: PCT/US2016/052533
§ 371 (c)(1),
(2) Date: Mar. 16, 2018

(87) PCT Pub. No.: WO2017/049308
PCT Pub. Date: Mar. 23, 2017

(65) Prior Publication Data
US 2018/0258207 A1 Sep. 13, 2018

Related U.S. Application Data

(60) Provisional application No. 62/219,745, filed on Sep. 17, 2015.

(51) Int. Cl.
| | | |
|---|---|---|
| *C08G 75/02* | (2016.01) |
| *C08G 75/20* | (2016.01) |
| *C08F 228/02* | (2006.01) |
| *C08G 85/00* | (2006.01) |
| *C08G 81/00* | (2006.01) |
| *C08G 75/23* | (2006.01) |
| *C08G 75/0286* | (2016.01) |
| *C08L 81/00* | (2006.01) |
| *C08G 75/00* | (2006.01) |
| *A61L 27/16* | (2006.01) |
| *A61L 29/04* | (2006.01) |
| *A61L 31/04* | (2006.01) |
| *C08F 236/04* | (2006.01) |
| *C08F 299/02* | (2006.01) |
| *C08K 5/41* | (2006.01) |
| *C08G 75/04* | (2016.01) |
| *C08G 75/045* | (2016.01) |
| *A61L 27/54* | (2006.01) |
| *A61L 29/16* | (2006.01) |
| *A61L 31/16* | (2006.01) |

(52) U.S. Cl.
CPC ............ *C08F 228/02* (2013.01); *A61L 27/16* (2013.01); *A61L 29/041* (2013.01); *A61L 31/048* (2013.01); *C08F 236/04* (2013.01); *C08F 299/022* (2013.01); *C08G 75/00* (2013.01); *C08G 75/0286* (2013.01); *C08G 75/23* (2013.01); *C08G 81/00* (2013.01); *C08G 85/004* (2013.01); *C08K 5/41* (2013.01); *C08L 81/00* (2013.01); *A61L 27/54* (2013.01); *A61L 29/16* (2013.01); *A61L 31/16* (2013.01); *C08F 2810/30* (2013.01); *C08G 75/02* (2013.01); *C08G 75/04* (2013.01); *C08G 75/045* (2013.01); *C08G 75/20* (2013.01)

(58) Field of Classification Search
None
See application file for complete search history.

(56) References Cited

U.S. PATENT DOCUMENTS

| | | | |
|---|---|---|---|
| 4,485,227 A | 11/1984 | Fox | |
| 5,854,383 A | 12/1998 | Erneta | |
| 2003/0144445 A1* | 7/2003 | Gross | .................. C08G 75/045 526/286 |
| 2004/0054113 A1 | 3/2004 | Benz | |
| 2008/0125857 A1 | 5/2008 | Roorda | |

(Continued)

FOREIGN PATENT DOCUMENTS

| | | | |
|---|---|---|---|
| WO | 2014100238 | 6/2014 | |
| WO | 2014138017 | 9/2014 | |
| WO | WO-2014138017 A1 * | 9/2014 | ............ C08F 110/10 |

OTHER PUBLICATIONS

Nuyken, O. "Telechelics via addition of dithiols onto alkadienes". Makromolekulare Chemie, Rapid Communications 1990, 11(8), 365-373. (Year: 1990).*

(Continued)

*Primary Examiner* — Richard A Huhn
(74) *Attorney, Agent, or Firm* — Pabst Patent Group LLP

(57) ABSTRACT

Polymers having mechanical properties approaching or exceeding commercial elastomers and engineering thermoplastics, but improved biostability, are described herein. In one embodiment, the polymers have a hard segment containing one or more disulfoxide or disulfone moieties and a soft segment connected to the hard segment to form an elastomeric polymer. The polymer is resistant to oxidation and/or hydrolytic degradation, particularly in vivo, which allows for the use of these materials in implants/devices which are implanted for an extended period of time. The ratio or percentage by weight of soft segment to hard segment can be varied based on the physical and mechanical properties of the desired device.

23 Claims, No Drawings

(56) References Cited

U.S. PATENT DOCUMENTS

2010/0222513 A1    9/2010  Arriola
2011/0045030 A1    2/2011  Desai
2012/0129076 A1    5/2012  Ichimura
2015/0315330 A1*  11/2015  Heath ................... C08G 59/14
                                                        525/530

OTHER PUBLICATIONS

International Search Report dated Dec. 16, 2016 (PCT/US2016/52533).

* cited by examiner

BIOSTABLE SEGMENTED ELASTOMERS AND THERMOPLASTICS AND METHODS OF MAKING AND USING THEREOF

CROSS-REFERENCE TO RELATED APPLICATION

This application is a National Phase application under 35 U.S.C. § 371 of PCT/US2016/052533, filed Sep. 19, 2016, which claims priority to and benefit of U.S. Provisional Application No. 62/219,745, filed Sep. 17, 2015, which is hereby incorporated herein by reference in its entirety.

FIELD OF THE INVENTION

This invention is in the field of polymeric materials having improved biostability and biocompatibility, particularly for use in long-term, dynamic implants.

BACKGROUND OF THE INVENTION

There is a continuing need for biostable elastomers having the necessary physical and mechanical properties for long-term, dynamic implants, such as cardiac pacing lead insulation, cardiac assist device bladders, synthetic heart valves, chronic, indwelling catheters, and other implants or devices subject to degradation in vivo. Current commercially used elastomers, such as polysiloxanes and polyurethanes, suffer from deficiencies that make them less than ideal. For example, highly crosslinked poly(dimethylsiloxanes) exhibit favorable long-term biostability but relatively poor mechanical properties. In contrast, polyurethanes exhibit excellent toughness characteristics. These materials, however, exhibit limited biostability because the linkages within the polymer (e.g., ether, ester, carbonate, linear siloxane, and urethane) are susceptible to chemical breakdown in vivo by oxidative or hydrolytic mechanisms.

There exists a need for materials that exhibit mechanical properties approaching, similar to, or exceeding polyurethane elastomers and engineering thermoplastics but are more resistant to degradation in vivo than these materials.

Therefore, it is an object of the invention to provide materials that exhibit mechanical properties approaching, similar to, or exceeding polyurethane elastomers and engineering thermoplastics but are more resistant to degradation in vivo than these materials and methods of making and using thereof.

SUMMARY OF THE INVENTION

Segmented polymers containing one or more hard segments and one or more soft segments and exhibiting elastomeric mechanical properties are described herein. The polymers contain a plurality of sulfide, sulfoxide, and/or sulfone moieties. These moieties can be introduced via the hard segments, the soft segments, or combinations thereof. The segmented polymers are prepared by reacting one or more functionalized soft segments and one or more functionalized hard segments wherein the hard and soft segments have two or more thiols and two or more olefinic groups in all combinations of hard and soft segments. For example, the soft segments can contain two or more thiol groups and the hard segments can contain two or more olefinic groups. In other embodiments, the soft segments contain two or more olefinic groups and the hard segments contain two or more thiol groups. In still other embodiments, the soft segment contains one or more thiol groups and one or more olefinic groups and the hard segment contains one or more thiol groups and one or more olefinic groups.

In one embodiment, the polymer has the formula $[AB]_m$ wherein each occurrence of A includes a soft segment (R) and is derived from the monomer HS—R—SH and each occurrence of B includes a hard segment (R') and is derived from one or more monomers having the formula $R_2R_1C\!=\!CR_3$—R'—$CR_3\!=\!CR_1R_2$, each occurrence of R is a soft segment;

each occurrence of R' is independently selected from the group substituted or unsubstituted alkyl, heteroalkyl, cycloalkyl, heterocycloalkyl, aryl, heteroaryl, biaryl, bi-heteroaryl, alkaryl, such as methylene-bis-phenyl, $SO_2$, $SO_2(aryl)_2$, SO, S, where aryl is substituted or unsubstituted aryl or heteroaryl;

each occurrence of $R_1$-$R_3$ is independently hydrogen, halogen, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, ether heterocyclyl, aromatic or heteroaromatic moieties, —$CF_3$, or —CN; and m is an integer value such that the molecular weight of the polymer $M_n$ is from about 15,000 to about 600,000 Daltons, preferably from about 40,000 to about 200,000 Daltons; and where m is a positive integer value of at least 4 such that the number average molecular weight of the polymer ($M_n$) is from about 15,000 to about 600,000 Daltons, preferably from about 40,000 to about 200,00 Daltons. Generally m is a positive integer in a range with a lower limit of 4 to 10 with an upper limit of about 1,000. Preferably m is a positive integer that ranges from 4 to 1,000; from 4 to 950; from 4 to 925; from 4 to 900; from 4 to 800; from 4 to 700; from 4 to 600; from 4 to 500; from 4 to 400; from 4 to 300; from 4 to 200; from 4 to 100; from 4 to 50; from 10 to 1,000; from 10 to 950; from 10 to 925; from 10 to 900; from 10 to 800; from 10 to 700; from 10 to 600; from 10 to 500; from 10 to 400; from 10 to 300; from 10 to 200; from 10 to 100; or from 10 to 50.

Generally each occurrence of the soft segment (R) is a hydrocarbon-containing or silicon-containing moiety. Preferably each hydrocarbon-containing or silicon-containing moiety in the segmented polymer has a molecular weight between about 500 Da and about 3,000 Da.

In another embodiment, the polymer has the formula:

$[AB]_m$ wherein each occurrence of A includes a soft segment (R) and is derived from the monomer $R_2R_1C\!=\!CR_3$—R—$CR_3\!=\!CR_1R_2$ and each occurrence of B includes a hard segment (R') and is derived from one or more monomers having the formula HS—R'—SH;

each occurrence of R is a soft segment;

each occurrence of R' is independently selected from the group substituted or unsubstituted alkyl, heteroalkyl, cycloalkyl, heterocycloalkyl, aryl, heteroaryl, biaryl, bi-heteroaryl, alkaryl, such as methylene-bis-phenyl, $SO_2$, $SO_2(aryl)_2$, SO, S, where aryl is substituted or unsubstituted aryl or heteroaryl;

each occurrence of $R_1$-$R_3$ is independently hydrogen, halogen, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, ether heterocyclyl, aromatic or heteroaromatic moieties, —CF$_3$, or —CN; and where m is an integer value such that the number average molecular weight of the polymer (M$_n$) is from about 15,000 to about 600,000 Daltons, preferably from about 40,000 to about 200,00 Daltons where m is a positive integer value of at least 4 such that the number average molecular weight of the polymer (M$_n$) is from about 15,000 to about 600,000 Daltons, preferably from about 40,000 to about 200,00 Daltons. Generally m is a positive integer in a range with a lower limit of 4 to 10 and an upper limit of about 1,000. Preferably m is a positive integer that ranges from 4 to 1,000; from 4 to 950; from 4 to 925; from 4 to 900; from 4 to 800; from 4 to 700; from 4 to 600; from 4 to 500; from 4 to 400; from 4 to 300; from 4 to 200; from 4 to 100; from 4 to 50; from 10 to 1,000; from 10 to 950; from 10 to 925; from 10 to 900; from 10 to 800; from 10 to 700; from 10 to 600; from 10 to 500; from 10 to 400; from 10 to 300; from 10 to 200; from 10 to 100; or from 10 to 50.

Generally each occurrence of the soft segment (R) is a hydrocarbon-containing or silicon-containing moiety. Preferably each hydrocarbon-containing or silicon-containing moiety in the segmented polymer has a molecular weight between about 500 Da and about 3,000 Da. In some aspects, the molecular weight is between about 600 Da and about 3,000 Da, inclusive, between about 700 Da and about 3,000 Da, inclusive, between about 800 Da and about 3,000 Da, inclusive, between about 900 Da and about 3,000 Da, inclusive, between about 1,500 Da and about 3,000 Da, inclusive, between about 2,000 and about 3,000 inclusive, between about 500 Da and about 2,500 Da, inclusive, between about 500 Da and about 2,000 Da, inclusive, between about 500 Da and about 1,500 Da, inclusive, or between about 500 Da and about 1,000 Da.

Alternatively, in another embodiment, the segmented polymer has the formula:

[AB]$_m$, wherein A comprises the soft segment and is derived from one or more monomers having the formula R$_2$R$_1$C=CR$_3$—R—SH, wherein B comprises the hard segment and is derived from one or more monomers having the formula R$_2$R$_1$C=CR$_3$—R'—SH, and R, R', R$_1$, R$_2$, R$_3$, and m are as described above.

Optionally in some embodiments, monomers A and/or B may be substituted with one more substituents that do not participate in the main chain or backbone forming reaction. In other embodiments, monomers A and/or B can contain one or more substituents that allow for crosslinking of the polymers chains. The substituents can be additional thiol and/or vinyl groups and or other reactive functional groups.

The segmented polymers are biostable. They are resistant to oxidation and/or hydrolytic degradation, particularly in vivo, which allows for the use of these materials in implants/devices that are implanted for an extended period of time. The percentage (by weight) of soft segment and hard segment in the polymer can be varied based on the desired physical and mechanical properties of the desired device. In some embodiments, the polymers contain approximately 20-80 wt % of soft segment, with the remainder of the polymer containing the hard segment. In some other embodiments, the polymers contain about 20%, 25%, 30%, 35%, 40%, 45%, 50%, 55%, 60%, 65%, 70%, 75%, or 80 wt % of soft segment.

Preferred properties of elastomers (i.e. segmented polymers) for implantable medical applications demonstrate a flex fatigue resistance of >1 million dynamic cycles, tensile strengths in excess of 1,500 psi, secant moduli of ~300-10, 000 psi at 100% elongation, and a Shore A hardness of 50-95. In certain embodiments the segmented polymers described herein have a Shore A hardness in the range of 60-90.

In some embodiments, the hard segment can be prepared by reacting monomers containing two or more olefinic groups with a monomer containing two or more thiol groups or a combination of thiol and olefinic groups. Any combination of monomers can be used, provided it results in a hard to soft segment ratio having the desired molecular weight/size and/or mechanical properties. The hard segment can be modified to have olefinic groups at the termini of the hard segment. The olefinic groups can be reacted with the thiol groups on the soft segment to form the sulfide containing polymer. A subsequent oxidation step or steps can result in formation of the sulfoxide or sulfone moieties. Some sulfide functional groups may be retained before use. Such sulfide groups may be oxidized in situ without chain scission to produce enhanced properties or performance. The sulfide oxidation process may provide enhanced mechanical properties such as stiffness and tensile strength over the initially-formed polymer.

The polymers described herein can be used to fabricate, in whole or in part, medical devices and implants, particularly those implanted in vivo. For implants that are in use for extended periods of time, the polymers used in the fabrication of such implants should be biostable, biocompatible, and/or hemocompatible and exhibit the necessary physical and mechanical properties over the desired time period.

In some embodiments, the polymers described herein are used to fabricate whole or in part long-term, dynamic implants. Examples of such implants include, but are not limited to, cardiac pacing lead insulation, cardiac assist device bladders, chronic, indwelling catheters, synthetic heart valves, vascular grafts, and the like.

In other embodiments, the polymers described herein can be used to prepare "engineering thermoplastics". "Engineering Thermoplastics" refers to a subset of plastic materials that are used in applications generally requiring higher performance in the areas of heat resistance, chemical resistance, impact, fire retardancy and/or mechanical strength. "Engineering Thermoplastics" are so named as they are processable by melt techniques and have properties in one or more areas that exhibit higher performance than softer or weaker materials and are suitable for applications that require engineering to design parts that perform in their intended use.

DETAILED DESCRIPTION OF THE INVENTION

I. Definitions

"Segmented polymer", as used herein, generally means a copolymer containing phase domains of microscopic or smaller size, with the domains constituted principally of single types of structural units. The types of domains in a segmented copolymer usually contain hard- and soft-segment phase domains.

"Hard segment", as used herein, refers to a monomeric, oligomeric, and/or polymeric segment or block that imparts rigidity and/or toughness to the resulting polymer.

"Soft segment", as used herein, refers to a monomeric, oligomeric, and/or polymeric segment or block that controls rigidity and strength and provides elasticity to the resulting polymer when attached to the hard segment. Elasticity is the recovery of an original dimension from strain (elongation) after a force of strain is removed. "Recovery," as used herein refers to a return of all or most of original shape (such as at least 50%, 60%, 70%, 80%, 90%, 91%, 92%, 93%, 94%, 95%, 96%, 97%, 98%, or 99% of the original shape) over a range of elongation (e.g., about 10%, 20%, 30%, 40%, or 50% elongation).

"Elastomer", as used herein, refers to a polymer that recovers most or all of its original shape after being subjected to a designated strain. An elastomer generally displays low Young's modulus and high failure strain compared with other materials.

"Biostable", as used herein, refers to the maintenance of performance properties of implants intended for long-term chronic use, e.g., for periods ranging months to years, depending on the design intent of the device.

"Hemocompatible," as used herein, refers to a substance or object that performs its desired function when introduced into an organism without inducing significant inflammatory response, cytotoxicity to blood cells, platelet adhesion, or thrombogenic responses. Hemocompatibility can be tested according to ISO 10993-4.

"Alkyl", as used herein, refers to the moieties of saturated or unsaturated aliphatic groups, including straight-chain alkyl groups, branched-chain alkyl groups, cycloalkyl (alicyclic) groups, alkyl substituted cycloalkyl groups, and cycloalkyl substituted alkyl groups. Unless otherwise indicated, a straight chain or branched chain alkyl typically has 40 or fewer carbon atoms in its backbone (e.g., $C_1$-$C_{40}$ for straight chain, $C_3$-$C_{40}$ for branched chain). Likewise, cycloalkyls can typically have from 3-10 carbon atoms in their ring structure. The ranges provided above are inclusive of all values between the minimum value and the maximum value. "Cycloalkyl" as used herein includes monocyclics, bicylics (e.g., fused rings), etc., that may contain one or more additional sites of unsaturation, e.g., pi bond but does not include aromatic compounds.

Unless the number of carbons is otherwise specified, "lower alkyl" as used herein means an alkyl group, as defined above, but having from one to ten carbons, preferably from one to six carbon atoms in its backbone structure. Likewise, "lower alkenyl" and "lower alkynyl" have similar chain lengths. Preferred alkyl groups for branched or hard chain segments are lower alkyls. The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms. If they are acyclic, they are usually named for the heteroatom, e.g., alkyl sulfides, alkyl amines, etc.

"Alkenyl" and "Alkynyl", as used herein, refer to unsaturated aliphatic groups containing, one or more double or triple bonds, respectively, analogous in length (e.g., $C_2$-$C_{30}$) and possible substitution to the alkyl groups described above. Alkenyl and alkynyl groups can react with the thiol groups on the hard and/or soft segment. Therefore, such groups can be introduced onto the hard and/or soft segment chain or as branches to facilitate crosslinking of the polymer chains. In embodiments where such crosslinking is not desired, alkenyl and/or alkynyl groups are not present (other than on the hard and/or soft segments to participate in the backbone forming reaction).

"Aryl," as used herein, refers to $C_5$-$C_{26}$-membered aromatic, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, for example, benzene, naphthalene, anthracene, phenanthrene, chrysene, pyrene, corannulene, coronene, etc.

"Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Alkylaryl", as used herein, refers to an alkyl group substituted with an aryl group (e.g., an aromatic or hetero aromatic group).

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof.

Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, $-CH_2-CF_3$, $-CCl_3$), $-CN$, aryl, heteroaryl, and combinations thereof.

"Halogen", as used herein, refers to fluorine, chlorine, bromine, or iodine.

The term "substituted" as used herein, refers to all permissible substituents of the compounds described herein. In some embodiments, the term "substituted" refers to functional groups that do not react with the thiols and/or olefins on the hard and soft segments that participate in the backbone forming reaction as described above. In other embodiments, groups which react with thiols and/or olefin, in addition to the groups on the hard and/or soft segment which participate in the backbone forming reactions, may be present to facilitate crosslinking of the polymer chains. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, and optionally include one or more heteroatoms such as oxygen, sulfur, or nitrogen grouping in linear, branched, or cyclic structural formats. Representative substituents include, but are not limited to, alkyl, alkenyl, alkynyl, aryl (e.g., phenyl), heteroaryl, halo, hydroxyl, alkoxy, aroxy (e.g., phenoxy), alkylthio, arylthio (e.g., phenylthio), cyano, isocyano, carbonyl (e.g., formyl, ketone, aldehyde, ester, anhydride, etc.), carboxyl, amino, imino, amido, nitro, sulfhydryl, sulfonyl, sulfonic acid, phosphoryl, phosphonyl, polyaryl, silyl, $C_3$-$C_{20}$ cyclic, heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence, kinetic and thermodynamic requirements of the substituted atom and the substituent, and that the substitution results in a stable compound, i.e. a compound that does not spontaneously undergo transformation such as by addition, condensation, rearrangement, cyclization, elimination, etc.

Numerical ranges disclosed herein disclose individually each possible number in such range, as well as any sub-ranges and combinations of sub-ranges encompassed therein. For example, a carbon range (i.e., $C_1$-$C_{10}$) is intended to disclose individually every possible carbon value and/or sub-range encompassed within. For example, a carbon length range of $C_1$-$C_{10}$ discloses $C_1$, $C_2$, $C_3$, $C_4$, $C_5$, $C_6$, $C_7$, $C_8$, $C_9$, and $C_{10}$, as well as discloses sub-ranges encompassed within, such as $C_2$-$C_9$, $C_3$-$C_8$, $C_1$-$C_5$, etc. Similarly, an integer value range of 1-10 discloses the individual values of 1, 2, 3, 4, 5, 6, 7, 8, and 10, as well as sub-ranges encompassed within. Further, a concentration range or weight percent range, such as from 1% to 2% by weight of the formulation discloses, the individual values and fractions thereof, such as 1%, 1.1%, 1.2%, 1.32%, 1.48% etc., as well as sub-ranges encompassed within.

II. Polymers

Segmented polymers containing one or more hard segments (B) and one or more soft segments (A) producing elastomeric mechanical properties are described herein. Generally, throughout a segmented polymer, each hard segment alternates with a soft segment (i.e. two hard segments (or two soft segments) are not bound directly to each other). The segmented polymers may contain two or more different hard segments and/or two or more different soft segments. Preferably, the total number of soft segments and the total number of hard segments are generally equal. The polymers contain a plurality of sulfide, sulfoxide, and/or sulfone moieties. These moieties can be introduced via the hard segments, the soft segments, or combinations thereof.

The segmented polymers described herein preferably recover most of their original shape (such as at least 50%, 60%, 70%, 80%, 90%, 91%, 92%, 93%, 94%, 95%, 96%, 97%, 98%, or 99% of their original shape) following elongation and release of the force of elongation, over a range of elongation (e.g., about 10%, 20%, 30%, 40%, or 50%, or greater than 50% elongation).

In contrast, high-modulus polymers produced from hard segments alone generally undergo a yield behavior (unrecoverable strain) at a low elongation (e.g., <10% elongation).

The segmented polymers are prepared by reacting one or more functionalized soft segments and one or more functionalized hard segments wherein the hard and soft segments have two or more thiols and two or more olefinic groups in all combinations of hard and soft segments. For example, the soft segments can contain two or more thiol groups and the hard segments can contain two or more olefinic groups. In other embodiments, the soft segments contain two or more olefinic groups and the hard segments contain two or more thiol groups. In still other embodiments, the soft segment contains one or more thiol groups and one or more olefinic groups and the hard segment contains one or more thiol groups and one or more olefinic groups.

In one embodiment, the polymer has the formula

[AB]$_m$ wherein each occurrence of A includes a soft segment (R) and is derived from the monomer HS—R—SH and each occurrence of B includes a hard segment (R') and is derived from one or more monomers having the formula $R_2R_1C=CR_3—R'—CR_3=CR_1R_2$.

wherein each occurrence of R is a soft segment;

wherein each occurrence of R' is independently selected from the group substituted or unsubstituted alkyl, heteroalkyl, cycloalkyl, heterocycloalkyl, aryl, heteroaryl, biaryl, bi-heteroaryl, alkaryl, such as methylene-bis-phenyl, $SO_2$, $SO_2(aryl)_2$, SO, S, where aryl is substituted or unsubstituted aryl or heteroaryl. In some embodiments, R' is a substituted or unsubstituted $C_1$-$C_{12}$ alkyl.

each occurrence of $R_1$, $R_2$, and $R_3$ is independently hydrogen, halogen, alkyl, aralkyl, alkenyl, alkynyl, cycloalkyl, hydroxyl, alkoxyl, amino, nitro, sulfhydryl, imino, amido, amino phosphonate, phosphinate, carbonyl, carboxyl, silyl, ether, alkylthio, sulfonyl, sulfonamido, ketone, aldehyde, ester, ether heterocyclyl, aromatic or heteroaromatic moieties, —$CF_3$, or —CN; and m is an integer value such that the molecular weight of the polymer $M_n$ is from about 15,000 to about 600,000 Daltons, preferably from about 40,000 to about 200,000 Daltons. Generally m is a positive integer in a range with a lower limit of 4 to 10 and an upper limit of about 1,000. Preferably m is a positive integer that ranges from 4 to 1,000; from 4 to 950; from 4 to 925; from 4 to 900; from 4 to 800; from 4 to 700; from 4 to 600; from 4 to 500; from 4 to 400; from 4 to 300; from 4 to 200; from 4 to 100; from 4 to 50; from 10 to 1,000; from 10 to 950; from 10 to 925; from 10 to 900; from 10 to 800; from 10 to 700; from 10 to 600; from 10 to 500; from 10 to 400; from 10 to 300; from 10 to 200; from 10 to 100; or from 10 to 50.

Generally each occurrence of the soft segment (R) is a hydrocarbon-containing or silicon-containing moiety. Preferably each hydrocarbon-containing or silicon-containing moiety in the segmented polymer has a molecular weight between about 500 Da and about 3,000 Da. In some aspects, the molecular weight is between about 600 Da and about 3,000 Da, inclusive, between about 700 Da and about 3,000 Da, inclusive, between about 800 Da and about 3,000 Da, inclusive, between about 900 Da and about 3,000 Da, inclusive, between about 1,500 Da and about 3,000 Da, inclusive, between about 2,000 and about 3,000 inclusive, between about 500 Da and about 2,500 Da, inclusive, between about 500 Da and about 2,000 Da, inclusive, between about 500 Da and about 1,500 Da, inclusive, or between about 500 Da and about 1,000 Da.

In another embodiment, the polymer has the formula:

[AB]$_m$ wherein each occurrence of A includes a soft segment (R) and is derived from the monomer $R_2R_1C=CR_3—R—CR_3=CR_1R_2$ and each occurrence of B includes a hard segment (R') and is derived from one or more monomers having the formula HS—R'—SH;

wherein each occurrence of R is a soft segment;

each occurrence of R' is independently selected from the group substituted or unsubstituted alkyl, heteroalkyl, cycloalkyl, heterocycloalkyl, aryl, heteroaryl, biaryl, bi-heteroaryl, alkaryl, such as methylene-bis-phenyl, $SO_2$, $SO_2$ (aryl)$_2$, SO, S, where aryl is substituted or unsubstituted aryl or heteroaryl. In some embodiments, R' is a substituted or unsubstituted $C_1$-$C_{12}$ alkyl.

each occurrence of $R_1$-$R_3$ is independently hydrogen, halogen, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, ether heterocyclyl, aromatic or heteroaromatic moieties, —$CF_3$, or —CN; and m is an integer value such that the molecular weight of the polymer $M_n$ is from about 15,000 to about 600,000 Daltons, preferably from about 40,000 to about 200,000 Daltons. Generally m is a positive integer in a range with a lower limit of 4 to 10 and an upper limit of about 1,000. Preferably m is a positive integer that ranges from 4 to 1,000; from 4 to 950; from 4 to 925; from 4 to 900; from 4 to 800; from 4 to 700; from 4 to 600; from 4 to 500; from 4 to 400; from 4 to 300; from 4 to 200; from 4 to 100; from 4 to 50; from 10 to 1,000; from 10 to 950; from 10 to 925; from 10 to 900; from 10 to 800; from 10 to 700; from 10 to 600; from 10 to 500; from 10 to 400; from 10 to 300; from 10 to 200; from 10 to 100; or from 10 to 50.

In another embodiment, the polymer has the formula:

[AB]$_m$ wherein each occurrence of A includes a soft segment (R) and is derived from the monomer $R_2R_1C=CR_3—R—SH$, wherein each occurrence of B includes a hard segment (R') and is derived from the monomer $R_2R_1C=CR_3—R'—SH$, wherein each occurrence of R is a soft segment;

each occurrence of R' is independently selected from the group consisting of substituted or unsubstituted alkyl, heteroalkyl, cycloalkyl, heterocycloalkyl, aryl, heteroaryl, biaryl, bi-heteroaryl, $SO_2$, $SO_2(aryl)_2$, where aryl is substituted or unsubstituted aryl or heteroaryl;

each occurrence of $R_1$, $R_2$, and $R_3$ is independently hydrogen, halogen, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, ether heterocyclyl, aromatic or heteroaromatic moieties, —$CF_3$, or —CN; and m is an integer value such that the molecular weight of the polymer $M_n$ is from about 15,000 to about 600,000 Daltons, preferably from about 40,000 to about 200,000 Daltons. Generally m is a positive integer in a range with a lower limit of 4 to 10 and an upper limit of about 1,000. Preferably m is a positive integer that ranges from 4 to 1,000; from 4 to 950; from 4 to 925; from 4 to 900; from 4 to 800; from 4 to 700; from 4 to 600; from 4 to 500; from 4 to 400; from 4 to 300; from 4 to 200; from 4 to 100; from 4 to 50; from 10 to 1,000; from 10 to 950; from 10 to 925; from 10 to 900; from 10 to 800; from 10 to 700; from 10 to 600; from 10 to 500; from 10 to 400; from 10 to 300; from 10 to 200; from 10 to 100; or from 10 to 50.

Generally each occurrence of the soft segment (R) is a hydrocarbon-containing or silicon-containing moiety. Preferably each hydrocarbon-containing or silicon-containing moiety in the segmented polymer has a molecular weight between about 500 Da and about 3,000 Da. In some aspects, the molecular weight is between about 600 Da and about 3,000 Da, inclusive, between about 700 Da and about 3,000 Da, inclusive, between about 800 Da and about 3,000 Da, inclusive, between about 900 Da and about 3,000 Da, inclusive, between about 1,500 Da and about 3,000 Da, inclusive, between about 2,000 and about 3,000 inclusive, between about 500 Da and about 2,500 Da, inclusive, between about 500 Da and about 2,000 Da, inclusive, between about 500 Da and about 1,500 Da, inclusive, or between about 500 Da and about 1,000 Da.

The polymers described herein are biostable; they are resistant to oxidation and/or hydrolytic degradation, particularly in vivo, which allows for the use of these materials in implants/devices which are implanted for an extended period of time. The percentage (by weight) of soft segment and hard segment in the polymer can be varied based on the physical and mechanical properties of the desired device. In some embodiments, the polymers contain approximately 20-80 wt % of soft segment. In some other embodiments, the polymers contain about 20%, 25%, 30%, 35%, 40%, 45%, 50%, 55%, 60%, 65%, 70%, 75%, or 80 wt % of soft segment.

The hard segment can be prepared by reacting monomers containing two or more vinyl groups with a short chain monomer containing two or more thiol groups and/or a combination of thiol and vinyl groups. The hard segment can be terminated with vinyl or thiol groups. The vinyl groups can be reacted with the thiol groups on the soft segment to form the polymer. Subsequent oxidation can result in formation of the sulfoxide or sulfone moieties without chain scission.

A. Soft Segment

The segmented polymers described herein contain one or more monomers "A" containing a soft segment. The soft segment provides elasticity to the segmented polymer when attached to a hard segment compared to a polymer of the same weight containing only the hard segment.

Generally each A in the segmented copolymer independently contains a hydrocarbon-containing or silicon-containing moiety. Preferably each hydrocarbon-containing or silicon-containing moiety has a molecular weight between about 500 Da and about 3,000 Da. In some aspects, the molecular weight is between about 600 Da and about 3,000 Da, inclusive, between about 700 Da and about 3,000 Da, inclusive, between about 800 Da and about 3,000 Da, inclusive, between about 900 Da and about 3,000 Da, inclusive, between about 1,500 Da and about 3,000 Da, inclusive, between about 2,000 and about 3,000 inclusive, between about 500 Da and about 2,500 Da, inclusive, between about 500 Da and about 2,000 Da, inclusive, between about 500 Da and about 1,500 Da, inclusive, or between about 500 Da and about 1,000 Da.

In some embodiments, the one or more monomers that form A in the segmented polymer are derived from monomers having the following formulae:

$R_2R_1C=CR_3-R-CR_3=CR_1R_2$ (e.g., when hard segments contain thiol groups), $R_2R_1C=CR_3-R-SH$ (e.g., when hard segments contain one or more thiol groups and one or more olefinic groups), and/or $HS-R-SH$ (e.g., when hard segments contains olefinic groups), wherein R is the soft segment, $R_1$, $R_2$ and $R_3$ are defined above.

The soft segment R can be any biostable, biocompatible soft segment known in the art. The soft segment can be a polymer or copolymer, an oligomer, or a monomer. Generally each occurrence of the soft segment (R) is a hydrocarbon-containing or silicon-containing moiety. Preferably each hydrocarbon-containing or silicon-containing moiety in the segmented polymer has a molecular weight between about 500 Da and about 3,000 Da, more preferably between about 540 Da and about 3,000 Da. In some aspects, the molecular weight is between about 600 Da and about 3,000 Da, inclusive, between about 700 Da and about 3,000 Da, inclusive, between about 800 Da and about 3,000 Da, inclusive, between about 900 Da and about 3,000 Da, inclusive, between about 1,500 Da and about 3,000 Da, inclusive, between about 2,000 and about 3,000 inclusive, between about 500 Da and about 2,500 Da, inclusive, between about 500 Da and about 2,000 Da, inclusive, between about 500 Da and about 1,500 Da, inclusive, or between about 500 Da and about 1,000 Da.

Exemplary soft segments include, but are not limited to, oligo- or polyisobutylene, fatty acids, fatty acid backbone, dimerized or oligomerized fatty acids, dimerized or oligomerized fatty acid backbones, oligo- or poly(styrene-isobutylene-styrene) (SIBS), oligo- or poly(dimethylsiloxane), oligo- or poly(fluorosilicone), polyethylene and copolymers thereof, polypropylene and copolymers thereof, atactic polypropylene and combinations thereof.

In those embodiments where the soft segments contain one or more sulfide groups, upon formation of the polymer, the sulfide groups can be oxidized to sulfoxides and/or sulfones. Sulfoxides are resistant to hydrolysis and sulfones are resistant to oxidation and hydrolysis and therefore provide improved biostability compared to current commercially used materials.

In some embodiments, the soft segment is poly(styrene-isobutylene-styrene) or SIBS. Methods of making SIBS are known in the art (see, e.g. U.S. Pat. Nos. 5,741,331, 6,102,939, and 6,197,240 to Leonard Pinchuk). The soft segments described herein must be "telechelic", i.e., terminated with reactive groups, such as a thiol or olefinic group in order to form covalent bonds with a hard segment. For example, if the hard segment contains a an olefinic group, such as a vinyl group, then A typically contains thiol groups and vice versa. Alternatively, A and B can contain at least one thiol group and at least one olefinic group.

B. Hard Segment

The segmented polymers described herein also contain one or more monomers "B" containing a hard segment (R'). In some embodiments, the one or more monomers that form B in the segmented polymer are derived from monomers having the following formulae:

$R_2R_1C=CR_3-R'-CR_3=CR_1R_2$ (e.g., when soft segments contain thiol groups), $R_2R_1C=CR_3-R'-SH$ (e.g., when soft segments contain one or more thiol groups and one or more olefinic groups), and/or $HS-R'-SH$ (e.g., when soft segments contains olefinic groups), wherein R' is selected from substituted or unsubstituted alkyl, heteroalkyl, cycloalkyl, heterocycloalkyl, aryl, heteroaryl, biaryl, bi-heteroaryl, $SO_2$, $SO_2(aryl)_2$, SO, and S, where aryl is substituted or unsubstituted aryl or heteroaryl, $R_1$-$R_3$ are defined above. In some embodiments, R' is a substituted or unsubstituted $C_1$-$C_{12}$ alkyl.

Preferably each hard segment containing monomer B has a molecular weight between about 50 Da and about 500 Da, preferably between about 100 Da and about 500 Da, more preferably between about 100 Da and about 300 Da.

In some embodiments, the hard segments contain a combination of an aromatic moiety and a short-chain aliphatic molecule. Such segments can be prepared by reacting an aromatic moiety-containing monomer with at least two reactive functional groups with a short aliphatic chain-containing monomer containing at least two reactive functional groups that react with the functional groups on the aromatic moiety-containing monomer. For example, the hard segment can be the reaction product of an aromatic-containing molecule, such as divinyl benzene and a short-chain aliphatic containing molecule, such as butane dithiol. Other segments include, but are not limited to, aliphatic linear or branched and/or cycloaliphatic short-chain divinyl-, dithio- and monovinyl/monothio molecules.

Exemplary monomers include, but are not limited to:

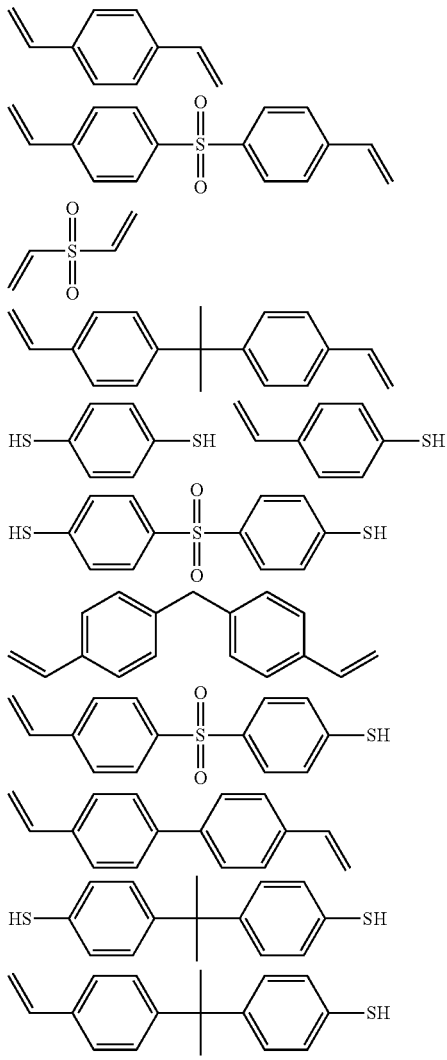

Other monomers include, but are not limited to, divinyl-, dithio-, monovinyl/monothio linear or branched aliphatic short-chain (e.g., less than 10, 8, 6, or 5 carbons) or cycloaliphatic molecules. In certain embodiments, monomers containing both thiol and vinyl groups, may be useful in forming hard segment oligomers which can be terminated by the addition of dithiol or divinyl hard segment-forming molecules.

The hard segment can be prepared by reacting any combination of the monomers described above to form the hard segment provided the combination of monomers contains at least two thiol groups and two vinyl groups. For example, a dithiol can be reacted with a diene to form a hard segment via chain extension Michael Addition. The segmented polymer can be formed in one, two, or more steps. Molecular weight can be controlled by unbalancing the thiol to vinyl stoichiometry, a technique familiar to those skilled in the art.

C. Segmented Polymer Properties

The segmented polymers described herein are biocompatible and are resistant to degradation, particularly in vivo (e.g., biostable), over an extended period of time, such as at least 1, 2, 3, 4, 5, 6, 8, 10, 12, 14, 16, 18, 20, 22, 24, 30, 36, 48, or 60 months or longer. In some other embodiments the polymers are also hemocompatible. In some embodiments, the polymers are biostable and hemocompatible over a period of at least 1, 2, 3, 4, 5, 6, 8, 10, 12, 14, 16, 18, 20, 22, 24, 30, 36, 48, or 60 months or longer. In still other embodiments, the period of time is in the approximate range of at least six months up to 1, 2, 3, 4, or 5 years or longer, such as until removal of the implant. Biostability may be predicted by aging the polymers in oxidizing and hydrolytic media. Preclinical long-term implant qualification studies may be run for two years or longer. Properties measured include, but are not limited to, mechanical properties, molecular weight, dimensional stability, and flex fatigue resistance.

The polymers described herein exhibit mechanical properties, such as toughness, approaching or exceeding polyurethanes. In some embodiments, the polymers described herein exhibit a tensile strength of at least about 1500, 2000, 2500, 3000, 3500, 4000, 4500, 5000, 5500, or 6000 psi or greater as measured by ASTM D412-61T, following an implantation period ranging from 1 day, 1 week, 1 month, 6 months, 1 year, 2 years, or 5 years, or any interval within the listed time periods. In some embodiments, the polymers described herein exhibit an elongation of at least 100, 200, 250, 300, 350, 400, 450, 500, 550, 600, 650, or 700% or greater as measured by ASTM D-412-61T, following an implantation period ranging from 1 day, 1 week, 1 month, 6 months, 1 year, 2 years, or 5 years, or any interval within the listed time periods. In some embodiments, the polymers described herein maintain a number average molecular weight of within 20, 15, 14, 13, 12, 11, 10, 9, 8, 7, 6, or 5% or less of the original molecular weight of the polymer, over a time period ranging from 1 day, 1 week, 1 month, 6 months, 1 year, 2 years, or 5 years, or any interval within the listed time periods. In some embodiments, the polymers described herein can pass at least about 1, 2, 5, 8, 10, 15, 20, 25, 30, 35, 40, 45, or 50 million or greater flexes, over a time period ranging from 1 day, 1 week, 1 month, 6 months, 1 year, 2 years, 5 year, or 10 years, or any interval within the listed time periods. Flex fatigue resistance can be evaluated using commercially available flexing fatigue testing equipment using known test methods to determine a material's ability to resist dynamic fatigue based on standards including, for example, ISO 132, ASTM D-430 "B"; ASTM D 813. In some embodiments two or more of the desired properties listed here are combined in a given polymer.

III. Methods of Making the Polymers

The segmented polymers can be prepared using techniques known in the art.

The hard segments can be prepared by reacting a combination of diene monomers with dithiols and/or thiol-enes to form a hard segment terminated with vinyl or thiol groups in a chain forming reaction via Michael addition to form sulfide bonds as shown below. The pre-polymer can be synthesized in solution, in the melt, or by reaction injection molding in one, two, or more steps.

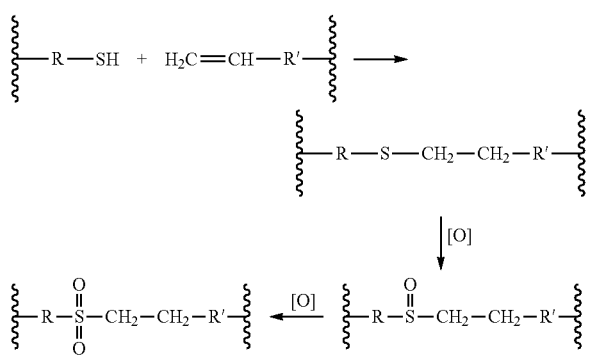

Once the hard segment pre-polymer is formed, the hard segment is reacted with the soft segments to form the polymer via the same chain forming reaction. Alternatively, the hard and soft segments can be formed/reacted simultaneously. The sulfides can be oxidized to sulfoxide or sulfone groups without chain cleavage.

Optionally, only a portion of the sulfur-linkages are oxidized (i.e, partial oxidation) to form a segmented polymer containing both sulfoxide and sulfone groups.

The hard and/or soft segments can be resistant to oxidative or hydrolytic chain cleavage. For example, segments formed essentially of, but not necessarily exclusively of, a hydrocarbon backbone structure are more hydrolytically stable than backbones containing esters and more oxidatively stable than those containing ethers. The physical and mechanical properties can be varied by varying the nature and/or amount of the hard and soft monomers. For example, varying the molar feed ratio of hard to soft monomers can produce materials ranging from soft to relatively hard elastomers.

IV. Method of Using the Polymers

The polymers described herein can be used to fabricate, in whole or in part, medical devices, particularly implants and topical devices. For implants intended for extended periods of time, the polymers used to fabricate the implants must be biostable over the desired time period and exhibit the necessary physical and mechanical properties over the desired time period. In some embodiments, the polymers described herein are used to fabricate whole or in part long-term, dynamic implants. Examples of such implants include, but are not limited to: cardiac pacing lead insulation, cardiac assist device bladders, synthetic heart valves, chronic, indwelling catheters, endoluminal scaffolds, stents, cartilage replacement devices, synthetic ligaments and tendons, and the like. In some embodiments, the polymer-based devices or implants are hard or soft tissue replacement devices, such as for replacing bone, cartilage, ligament, and/or tendon. In certain other embodiments, the polymer-based devices or implants form, in whole or in part, a component that adds structural support to medical devices, such as synthetic vascular grafts.

Incorporation and Release of Bioactive Agents

In certain embodiments, device(s) fabricated in whole or in part from the polymers described herein may be topically applied or applied as an external applique. Examples where such devices may be applied topically or externally include, but are not limited to, bandages, patches, dressings, tape, wraps, films, and the like. In some other embodiments, the device(s) fabricated in whole or in part from the polymers described herein may be applied or affixed to a naturally or non-naturally occurring bodily orifice. Examples of such devices or components include, but are not limited to, ostomy appliances, bandages, patches, dressings, tape, wraps, films, electrode components and the like.

In some embodiments, medical devices that are fabricated, in whole or in part, from the polymers described herein also include without limitation one or more bioactive agents, such as a drug, peptide, gene therapy agent, cell, biologic, or a combination thereof. The bioactive agent may form part of the polymer that forms the device, may be incorporated inside the device, and/or may be applied on a surface of the device. A device which includes a bioactive agent may also include a means of releasing the bioactive agent from the device in a controllable or sustainable manner.

The bioactive agent may be added during the preparation of polymeric compositions, or may be added after the polymeric composition is formed, optionally after the device is formed.

Exemplary bioactive agents include, but are not limited to, drugs, peptides, proteins, gene therapy agents, cells, biologics, and combinations thereof.

Exemplary classes of bioactive agents include therapeutic, prophylactic and diagnostic agents. For example, the bioactive agent may be a small molecule drug, a biologic drug, a vaccine, a protein, an antibody or other biological macromolecule. The bioactive agent may be a mixture of two or more different compounds, such as those listed above.

Exemplary bioactive agents include, but are not limited to, tumor antigens, CD4+ T-cell epitopes, cytokines, chemotherapeutic agents, radionuclides, small molecule signal transduction inhibitors, photothermal antennas, monoclonal antibodies, immunologic danger signaling molecules, other immunotherapeutics, enzymes, antibiotics, antivirals (especially protease inhibitors alone or in combination with nucleosides for treatment of HIV or Hepatitis B or C), anti-parasites (helminths, protozoans), growth factors (e.g. members of the TGFβ superfamily), growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors (including but not limited to CpG oligonucleotides) to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of microparticles into cells (including dendritic cells and other antigen-presenting cells), nutraceuticals such as vitamins, and oligonucleotide drugs (including DNA, RNAs, antisense, aptamers, small interfering RNAs (siRNA), ribozymes, external guide sequences for ribonuclease P, and triplex forming agents).

Exemplary diagnostic agents include paramagnetic molecules, fluorescent compounds, magnetic molecules, and radionuclides, x-ray imaging agents, drugs to induce analyzable responses, and contrast agents.

The bioactive agent may be one or more immunomodulatory agents. Exemplary immunomodulatory agents include cytokines, xanthines, interleukins, interferons, oligodeoxynucleotides, glucans, growth factors (e.g., TNF, CSF, GM- CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

Examples of immunological adjuvants that can be associated with the matrix include, but are not limited to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives there of including, but not limited to, monophosphoryl lipid A (MPL), glycopyranosyl lipid A, PET-lipid A, and 3-O-desacyl-4'-monophosphoryl lipid A. In a specific embodiment, the immunological adjuvant is MPL. In another embodiment, the immunological adjuvant is LPS. TLR ligands can also include, but not limited to, TLR3 ligands (e.g., polyinosinic-polycytidylic acid (poly(I:C)), TLR7 ligands (e.g., imiquimod and resiquimod), and TLR9 ligands.

As used herein, drugs are organic or inorganic molecules, including proteins, nucleic acids, polysaccharides and synthetic organic molecules, having a bioactive effect, for example, anaesthetics, vaccines, chemotherapeutic agents, hormones, metabolites, sugars, immunomodulators, antioxidants, ion channel regulators, and antibiotics. Exemplary small molecules include, but are not limited to, steroids, anthracyclines such as doxorubicin and daunorubicin, sulfasalazine, griseofulvin and related compounds such as griseoverdin; some anti-malaria drugs (e.g. Atovaquone); immune system modulators (e.g. cyclosporine); and cardiovascular drugs (e.g. digoxin and spironolactone); and ibuprofen (analgesic); ritonavir, nevirapine, lopinavir (antiviral); clofazinine (leprostatic); diloxanide furoate (antiamebic); glibenclamide (anti-diabetes); nifedipine (anti-anginal); spironolactone (diuretic); steroidal drugs such as danazol; carbamazepine, and anti-virals such as acyclovir. Other small molecules include acetazolamide, allopurinol, dapsone, doxycycline, paracetamol, nalidixic acid, clorothiazide, tobramycin, cyclosporin, tacrolimus, and paclitaxel.

As used herein peptides, or salts, analogs, and/or mixtures thereof refer to, but are not limited to, glucagon, pramlintide, insulin, leuprolide, an luteinizing-hormone-releasing hormone (LHRH) agonist, parathyroid hormone (PTH) or its pharmaceutically active sub-units, amylin, botulinum toxin, hematide, an amyloid peptide, cholecystikinin, gastric inhibitory peptide, an insulin-like growth factor, growth hormone releasing factor, anti-microbial factor, glatiramer, glucagon-like peptide-1 (GLP-1), a GLP-1 agonist, e.g., exenatide, interferons, insulin, insulin analogs, c-peptide, amylin, analogs thereof, and mixtures thereof.

Cells may be chosen based on a desired therapeutic effect. Cells can include, but are not limited to, autologous cells, allogeneic cells, or xenogeneic cells. Cells can be obtained from natural sources, stem cells, derived cells, or genetically engineered cells. In some embodiments, the cells can secrete a therapeutically effective substance, such as a protein or nucleic acid. In some embodiments, the cells can produce a metabolic product. In some embodiments, the cells can metabolize toxic substances. Cells can be cultured using techniques known to those skilled in the art of tissue culture.

As used herein, a "gene" is an isolated nucleic acid molecule of greater than thirty nucleotides, preferably one hundred nucleotides or more, in length. A gene therapy agent may be used in a treatment or method, wherein genes are released or delivered from the polymers described herein and device(s) fabricated, in whole or in part, therefrom.

Gene therapy methods can be applied to any gene. Exemplary genes include, but are not limited to, HGF gene, TGF-β gene, HSP gene, VEGF gene, FGF gene, EGF gene and so on.

The polymers described herein can be used as elastomers in dynamic or static implant applications. The polymers can also be fabricated in order to approach the rigidity and strength of engineering thermoplastics, and, due to their compositional versatility, may offer advantages over commercially available engineering thermoplastic polysulfones in certain products that benefit from the application of such tailored properties when applied to specific products such as bone and cartilage replacement devices vascular graft reinforcing coils, stents, etc.

The polymers described herein can be used alone or in combination with additional polymeric materials (e.g., blends) and/or additives. Exemplary classes of additives include, but are not limited to, plasticizers, stabilizers (e.g., heat and/or UV), colorants, various fillers, such as minerals and/or fibers, that are added for stiffness, strength, impact or some other performance feature like electrostatic dissipation, lubricity or thermal conductivity, and combinations thereof.

We claim:
1. A segmented copolymer comprising
a backbone comprising
a plurality of hard segment units and
a plurality of soft segment units,
wherein each unit of the hard segment units has a molecular weight between about 50 Da and about 500 Da,
wherein each unit of the soft segment units has a molecular weight between about 600 Da and about 3000 Da,
wherein the plurality of soft segment units provides elasticity when covalently bonded to the hard segment units,
wherein one or more units of the hard segment units are covalently bonded to one or more units of the soft segment units via a sulfone moiety, and
wherein each unit of the hard segment units and the soft segment units is derived from a difunctional monomer selected from the group consisting of divinyl, dithiol, and monovinyl/monthiol monomers.

2. The segmented copolymer of claim 1, wherein one or more units of the hard segment units are covalently bonded to one or more units of the soft segment units via a sulfoxide moiety.

3. The segmented copolymer of claim 1, wherein each unit of the hard segment units has a molecular weight between about 100 Da and about 300 Da.

4. The segmented copolymer of claim 1, wherein each unit of the hard segment units is derived from an aliphatic linear, aliphatic branched, aromatic, or cycloaliphatic short-chain molecule.

5. The segmented copolymer of claim 1, wherein each unit of the soft segment units comprises a hydrocarbon-containing or a silicon-containing moiety.

6. The segmented copolymer of claim 1, wherein the backbone does not contain a functional group that allows for crosslinking.

7. The segmented copolymer of claim 1, wherein the segmented copolymer has the formula:

$$[AB]_m$$

wherein A comprises the soft segment unit and is derived from one or more monomers having the formula HS—R—SH, and wherein B comprises the hard segment unit and is derived from one or more monomers having the formula $R_2R_1C=CR_3—R'—CR_3=CR_1R_2$, wherein each occurrence of R is independently a hydrocarbon-containing or silicon-containing moiety;

wherein each occurrence of R' is independently selected from the group consisting of substituted or unsubstituted alkyl, heteroalkyl, cycloalkyl, heterocycloalkyl, aryl, heteroaryl, biaryl, bi-heteroaryl, $SO_2$, $SO_2(aryl)_2$, where aryl is substituted or unsubstituted aryl or heteroaryl;

wherein each occurrence of $R_1$, $R_2$, and $R_3$ is independently hydrogen, halogen, alkyl, aralkyl, cycloalkyl, alkoxyl, nitro, amido, phosphonate, sulfonyl, sulfonamido, ketone, ester, aromatic or heteroaromatic moieties, or $CF_3$; and wherein m is an integer value between 4 and 1,000, inclusive, and wherein the number average molecular weight of the polymer (Mn) is from about 15,000 to about 600,000 Daltons.

8. The segmented copolymer of claim 7, wherein each hydrocarbon-containing or silicon-containing moiety has a molecular weight between about 600 Da and about 3,000 Da.

9. The segmented copolymer of claim 7, wherein each R is independently selected from the group consisting of polyisobutylene, fatty acid, dimerized fatty acid, oligomerized fatty acid, polyethylene, polyethylene copolymers, polypropylene, polypropylene copolymers, poly(styrene-isobutylene-styrene), poly(dimethylsiloxane), and poly(fluorosilicone), or combinations thereof.

10. The segmented copolymer of claim 9, wherein R' is a substituted or unsubstituted $C_1$-$C_{12}$ alkyl.

11. The segmented copolymer of claim 1, wherein the segmented copolymer has the formula:

$[AB]_m$ wherein A comprises the soft segment unit and is derived from one or more monomers having the formula $R_2R_1C=CR_3—R—CR_3=CR_1R_2$, and wherein B comprises the hard segment unit and is derived from one or more monomers having the formula HS—R'—SH, wherein each occurrence of R is a hydrocarbon-containing or silicon-containing moiety;

wherein each occurrence of R' is independently selected from the group consisting of substituted or unsubstituted alkyl, heteroalkyl, cycloalkyl, heterocycloalkyl, aryl, heteroaryl, biaryl, bi-heteroaryl, $SO_2$, $SO_2(aryl)_2$, where aryl is substituted or unsubstituted aryl or heteroaryl;

wherein each occurrence of $R_1$, $R_2$, and $R_3$ is independently hydrogen, halogen, alkyl, aralkyl, cycloalkyl, alkoxyl, nitro, amido, phosphonate, sulfonyl, sulfonamido, ketone, ester, aromatic or heteroaromatic moieties, or —$CF_3$; and wherein m is an integer value between 4 and 1,000, inclusive, and wherein the number average molecular weight of the polymer (Mn) is from about 15,000 to about 600,000 Daltons.

12. The segmented copolymer of claim 11, wherein each hydrocarbon-containing or silicon-containing moiety has a molecular weight between about 500 Da and about 3,000 Da.

13. The segmented copolymer of claim 1, wherein the segmented copolymer has the formula:

$[AB]_m$ wherein A comprises the soft segment unit and is derived from one or more monomers having the formula $R_2R_1C=CR_3—R—SH$, wherein B comprises the hard segment unit and is derived from one or more monomers having the formula $R_2R_1C=CR_3—R'—SH$, wherein each occurrence of R is a hydrocarbon-containing or silicon-containing moiety;

wherein each occurrence of R' is independently selected from the group consisting of substituted or unsubstituted alkyl, heteroalkyl, cycloalkyl, heterocycloalkyl, aryl, heteroaryl, biaryl, bi-heteroaryl, $SO_2$, $SO_2(aryl)_2$, where aryl is substituted or unsubstituted aryl or heteroaryl;

each occurrence of $R_1$, $R_2$, and $R_3$ is independently hydrogen, halogen, alkyl, aralkyl, cycloalkyl, alkoxyl, nitro, amido, phosphonate, sulfonyl, sulfonamido, ketone, ester, aromatic or heteroaromatic moieties, or —$CF_3$;

wherein m is an integer value between 4 and 1,000, inclusive; and wherein the number average molecular weight of the polymer (Mn) is from about 15,000 to about 600,000 Daltons.

14. The segmented copolymer of claim 13, wherein each hydrocarbon-containing or silicon-containing moiety has a molecular weight between about 500 Da and about 3,000 Da.

15. A medical device comprising a segmented copolymer comprising
a backbone comprising
a plurality of hard segment units and a plurality of soft segment units,
wherein each unit of the hard segment units has a molecular weight between about 50 Da and about 500 Da,
wherein each unit of the soft segment units has a molecular weight between about 600 Da and about 3000 Da,
wherein the plurality of soft segment units provides elasticity when covalently bonded to the hard segment units,
wherein one or more units of the hard segment units are covalently bonded to one or more units of the soft segment units via a sulfone moiety, and
wherein each unit of the hard segment units and the soft segment units is derived from a difunctional monomer selected from the group consisting of divinyl, dithiol, and monovinyl/monthiol monomers.

16. The device of claim 15, wherein the device further comprises a bioactive agent.

17. The device of claim 15, wherein the device is implantable.

18. The device of claim 15, wherein the device is cardiac pacing lead insulation or a cardiac device.

19. The device of claim 18, wherein the device is a cardiac device and wherein the cardiac device is a cardiac assist device or a component thereof, or a component of a circulatory assist device, a catheter, an endoluminal scaffold or stent, or a synthetic heart valve.

20. The device of claim 19, wherein the cardiac device is a component of a cardiac assist device, and wherein the component is a bladder.

21. The device of claim 15, wherein the device is a hard or soft tissue replacement device.

22. The device of claim 21, wherein the device is a replacement for bone, cartilage, ligament, and/or tendon.

23. The device of claim 15, wherein the device is a synthetic vascular graft.

* * * * *